United States Patent

Kujundžić et al.

Patent Number: 5,854,219
Date of Patent: Dec. 29, 1998

[54] 9-N-ETHENYL DERIVATIVES OF 9(S)-ERYTHROMYCYLAMINE

[75] Inventors: Nedjeljko Kujundžić; Dina Pavlović; Gabrijela Kobrehel; Gorjana Lazarevski; Željko Kelnerić, all of Zagreb, Croatia

[73] Assignee: PLIVA, farmaceutska, kemijska, prehrambena i kozmeticka industrija, dionicko drustvo, Zagreb, Croatia

[21] Appl. No.: 956,352

[22] Filed: Oct. 23, 1997

[30] Foreign Application Priority Data

Oct. 28, 1996 [HR] Croatia .................. P960497A

[51] Int. Cl.⁶ .......... A61K 31/70; C07H 17/08; C07G 11/00; C07D 315/00
[52] U.S. Cl. .............. 514/29; 536/4.1; 536/7.2; 536/7.4; 536/7.5; 549/415
[58] Field of Search .............. 514/29; 536/4.1, 536/7.2, 7.4, 7.5

[56] References Cited

U.S. PATENT DOCUMENTS 3,794,635  2/1974  Evans .................. 260/210 E

Primary Examiner—Johann Richter
Assistant Examiner—Jane C. Oswecki
Attorney, Agent, or Firm—Pollock, Vande Sande & Amernick

[57] ABSTRACT

The invention relates to 9-N-ethenyl derivatives of 9 (S)-erythromycylamine, new semisynthetic antibiotics of the macrolide class of the general formula (I)

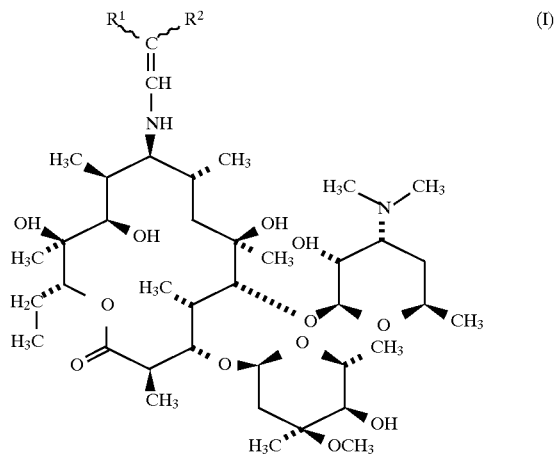

wherein $R^1$ and $R^2$ are the same or different and represent nitryl, a carboxyl group of the formula $COOR^3$, wherein $R^3$ represents a $C_1$–$C_4$ alkyl group, or a keto group of the formula $COR^4$, wherein $R^4$ represents a $C_1$–$C_4$ alkyl group, to their pharmaceutically acceptable addition salts with inorganic or organic acids, to a process for their preparation, to a process for the preparation of the pharmaceutical compositions as well as to the use of the obtained pharmaceutical compositions in the treatment of bacterial infections.

18 Claims, No Drawings

9-N-ETHENYL DERIVATIVES OF 9(S)-ERYTHROMYCYLAMINE

TECHNICAL FIELD

International Patent Classification: C 07 H 17/08, A 61 K 31/71

TECHNICAL PROBLEM

The present invention relates to 9-N-Ethenyl derivatives of 9(S)-erythromycylamine, novel semisynthetic antibiotics of the macrolide class having antibacterial action, of the general formula (I)

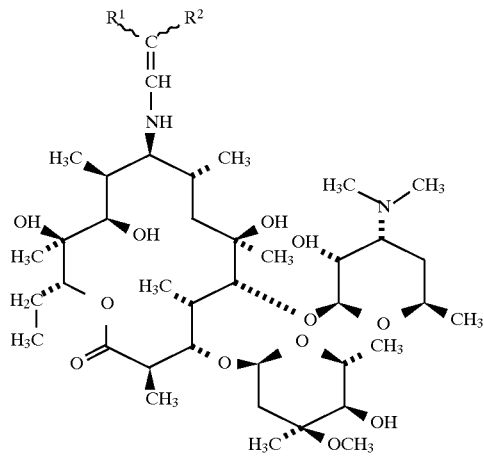

wherein $R^1$ and $R^2$ are the same or different and represent nitryl, a carboxyl group of the formula $COOR^3$, wherein $R^3$ represents a $C_1$–$C_4$ alkyl group, or a keto group of the formula $COR^4$, wherein $R^4$ represents a $C_1$–$C_4$ alkyl group, their pharmaceutically acceptable addition salts with inorganic or organic acids, to a process for the preparation thereof, to a process for the preparation of pharmaceutical compositions as well as to the use of the obtained pharmaceutical compositions in the treatment of bacterial infections.

PRIOR ART

Erythromycin A is a macrolide antibiotic, whose structure is characterized by a 14-member macrolactone ring having a carbonyl group in C-9 position. It was found by McGuire in 1952 (Antibiot. Chemother., 1952; 2:281) and for over 40 years it has been considered as a reliable and effective antimicrobial agent in the treatment of diseases caused by gram-positive and some gram-negative microorganisms. However, in an acidic medium it is easily converted into anhydroerythromycin, an inactive C-6/C-12 metabolite of a spiroketal structure (Kurath P. et al., Experientia 1971; 27:362). It is well-known that spirocyclisation of the aglycone ring of erythromycin A is successfully inhibited by a chemical transformation of C-9 ketones or of hydroxy groups in C-6 and/or C-12 positions. By the oximation of C-9 ketones (Đjokić S. et al., Tetrahedron Lett., 1967; 1945) and by subsequently modifying the obtained 9(E)-oxime into 9-[O-(2-methoxyethoxy)-methyloxime] erithromycin A (ROXITHROMYCIN) (Ambrieres, G. S., FR 2,473,525/1981) or 9(S)-erythromycylamine (Egan R. S. et al., J. Org. Chem., 1974; 39:2492) or a more complex oxazine derivative thereof, 9-deoxo-11-deoxy-9,11-{imino[2-(2-methoxyethoxyethylidene]-oxy}-9(S)-erythromycin A (DIRITHROMYCIN) (Lugar P. et al., J. Crist. Mol. Struct., 1979; 9:329), novel semisynthetic macrolides were synthetized, whose basic characteristic, in addition to a greater stability in an acidic medium, is better pharmacokinetics and a longer biological half-life with regard to the parent antibiotic erythromycin A.

The first successful synthesis of erythromycylamine by catalytical reduction of erythromycin oxime in glacial acetic acid with platinum oxide was performed by Massey et al. (Tetrahedron Lett., 1970, 157) and beside 9(S)-isomer also the less active 9(R)-isomer (Massey E. H. et al., J.Med.Chem. 1974, 17, 105) was obtained.

Kobrehel et al. (J.Med.Chem., 1978, 13, 83) synthesized a series of N-substituted benzensulfopylerythromycylamines. 11,12-Cyclic carbonates (Boyarska-Dahlig H. et al., Pol.J.Chem., 1979, 53, 2551; Sciavolino F. C., U.S. Pat. No. 4,283,527/1982) were prepared by treating erythromycylamine with ethylene carbonate via a previous protection of 9(S)-amino group. By the synthesis of peptide erythromycylamine (LeMahieu R. A. et al., J.Antib., 1982, 35, 10631) erythromycylamine derivatives without any antibiotic activity were obtained. Most research on erythromycylamine has included the reaction of erythromycylamine with aldehydes and ketones, whereat condensation products (Massey E. H. et al., J.Med.Chem., 1974, 17, 105) or 9-N-,11-O-oxazine derivatives (Maier R. et al., U.S. Pat. No. 4,048,306/1977) were obtained. By the reduction of the condensation product with $NaBH_4$, 9-N-alkyl or 9-N-benzyl derivatives (Wildsmith E. et al, J.Med.Chem. 1973; 16; 1059) were formed, 9-N, 11-O-oxazine derivatives, which are not reducible, being an exception.

Photoactive eiythromycylamine derivatives were prepared in the year 1989 by coupling photoreactive groups to erythromycylamine (Arevalo M. A. et al., J.Med.Chem., 1989, 32, 2200). In addition also a number of Schiff's bases of erythromycylamine were prepared (Aries R., FR appln. 2311029-1976; Ewans D., GB patent 1,345,524/1974; Werner R. G. et al., Biochem. Biophys. Res. Commun. 1978, 83, 1147).

According to the known and established prior art, there have not yet been described 9-N-ethenyl derivatives of 9-(S)-erythromycylamine and pharmaceutically acceptable addition salts thereof with inorganic or organic acids, a process for the preparation thereof as well as the preparation methods and use as pharmaceutical preparations.

It has been found and it is an object of the present invention that 9-N-ethenyl derivatives of 9-(S)-erythromycylamine and pharmaceutically acceptable addition salts thereof with inorganic or organic acids may be prepared by reacting 9-(S)-erythromycylamine with substituted etoxymethylene derivatives and, if appropriate, by reacting the obtained 9-N-ethenyl derivatives of 9-(S)-erythromycylamirie with inorganic or organic acids.

TECHNICAL SOLUTION

It has been found that 9-N-ethenyl derivatives of 9-(S)-erythromycylamine of the general formula (I)

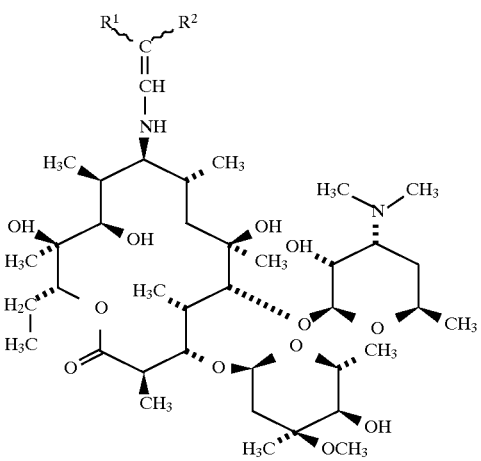

(I)

wherein $R^1$ and $R^2$ are the same or different and represent nitryl, a carboxyl group of the formula $COOR^3$, wherein $R^3$ represents a $C_1$–$C_4$ alkyl group, or keto group of the formula $COR^4$, wherein $R^4$ represents a $C_1$–$C_4$ alkyl group, and their pharmaceutically acceptable addition salts with inorganic or organic acids can be prepared by reacting 9-(S)-erythromycylamine of the formula (II)

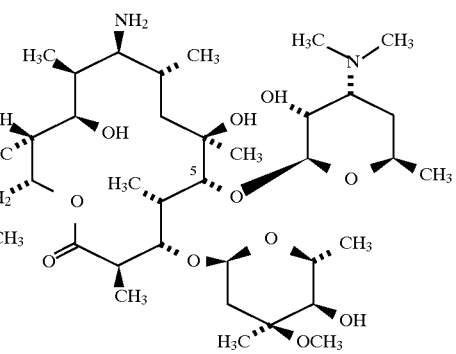

(II)

with etoxyethylene derivatives of the general formula (III)

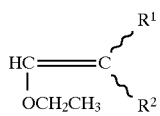

(III)

wherein $R^1$ and $R^2$ are the same or different and represent nitryl, a carboxyl group of the formula $COOR^3$, wherein $R^3$ represents a $C_1$–$C_4$ alkyl group, or a keto group of the formula $COR^4$, wherein $R^4$ represents a $C_1$–$C_4$ alkyl group. The reaction is carried out in toluene, xylene or some other aprotic solvent at a temperature from 20° to 80° C.

Pharmaceutically acceptable addition salts, which are also an object of the present invention, are obtained by the reaction of 9-N-ethenyl derivative of 9-(S)-erythromycylamine with an equimolar amount of an appropriate inorganic or organic acid such as hydrochloric acid, hydriodic acid, sulfuric acid, phosphoric acid, acetic acid, trifluoroacetic acid, propionic acid, benzoic acid, benzene sulfonic acid, methane sulfonic acid, lauryl sulfonic acid, stearic acid, palmitic acid, succinic acid, ethylsuccinic acid, lactobionic acid, oxalic acid, salicylic acid and similar acids, in a solvent inert to the reaction.

Compounds of the general formula (I), $R^1$, $R^2$, $R^3$ and $R^4$ have the meanings as defined hereinbefore demonstrate antibacterial in vitro action and their action spectrum is similar to the one of erthromycin. Hence they can be used for the same purpose and in the same manner as erythromycin A.

In general, compounds of the general formula (I) demonstrate in vitro action against Gram-positive microorganisms such as *Streptococcus faecalis* ATCC 8043, S. epidermidis ATCC 12228 and *Staphyococcus aureus* ATCC 6538. Their action is determined by the method of the dilution on microplates according to the protocol of the National Committee for Clinical Laboratory Standards (NCCLS, M7-A2). The obtained results expressed as MIC in mcg/ml suggest a potential use thereof as sterilisation agents of e.g. rooms and medical instruments and as industrial microbial agents e.g. for the protection of wall and wooden coatings.

The process for the preparation of 9-N-ethenyl derivatives of 9-(S)-erythromycylamine is illustrated by the following Examples which do not limit the scope of the invention in any way.

EXAMPLE 1

9(S)-N-(β,β-dicarbetoxyethenyl)erythromycylamine

A mixture of 9(S)-erythromycylamine (1.0 g; 1.36 mmol) and diethylethoxy methylenemalonate (3.2 ml; 16.0 mmol) was heated under reflux for 90 minutes. To the reaction mixture cooled to a temperature of 0°–5° C. diethylether (14 ml) was added and the obtained suspension was stirred for 15 minutes at the same temperature and for further 15 minutes at room temperature. 0.480 g of 9(S)-N-(β,β-dicarbetoxyethenyl) erythromycylamine were obtained.

The sample for analysis and biological investigation was purified by chromatography over a silica gel column in a solvent system $CHCl_3$:MEOH=9:1 yielding 0.27 g of 9(S)-N-(β,β-dicarbetoxyethenyl)erythromycylamine with the following physical-chemical constants:

IR ($CHCl_3$) cm$^{-1}$: 3500, 2950, 1725, 1670, 1600, 1450, 1380, 1250, 1225, 1170, 1080;

$^1$H NMR (300 MHz, $CDCl_3$) δ: 9.55 (1H, 9-N<u>H</u>—CH), 7.79 (9-NH—C<u>H</u>=C), 5.09 (1H, H-1"), 4.65 (1H, H-1'), 4.23 (—COOC<u>H</u>$_2$CH$_3$), 4.22 (1H, H-3), 4.17 (—COO C<u>H</u>$_2$CH$_3$), 3.35 (1H, H-5), 3.34 (3H, 3"-OCH$_3$), 3.28 (1H, H-2'), 3.06 (1H, H-4"), 2.65 (1H, H-9), 2.31 6H, 3'-N (CH$_3$)$_2$], 2.26 (1H, H-10), 1.96 (1H, H-8), 1.32 and 1.28 (—COOCH$_2$C<u>H</u>$_3$), 1.16 (3H, 8-CH$_3$), 1.06 (3H, 10-CH$_3$);

$^{13}$C NMR (75 MHz, $CDCl_3$) δ: 177.7 (C-1), 168.7 (—<u>C</u>OOCH$_2$CH$_3$), 166.7 (—<u>C</u>OOCH$_2$CH$_3$), 160.2 (9-NH—<u>C</u>H=C), 132.2 (9-NH—CH=C), 102.2 (C-1'), 95.7 (C-1"), 81.5 (C-5), 79.4 (C-3), 59.2 (—COO<u>C</u>H$_2$CH$_3$), 59.1 (—COO<u>C</u>H$_2$CH$_3$), 77.3 (C-4"), 70.5 (C-2'), 74.7 (C-9), 48.9 (3"-OCH$_3$), 40.0 [3'-N(CH$_3$)$_2$], 32.3 (C-10), 32.3 (C-8), 18.3 (8-CH$_3$), 14.1 (—COOCH$_2$<u>C</u>H$_3$), 13.9 (—COOCH$_2$<u>C</u>H$_3$), 13.0 (10-CH$_3$);

FAB-MS m/z 906 (M+H)$^+$.

EXAMPLE 2

9(S)-N-(β-cyano-β-carbetoxyethenyl) erythromycylamine

A mixture of 9 (S)-erythromycylamine (0.5 g; 0.68 mmol) and ethylethoxy methylene cyano acetate (0.2 g; 1.18 mmol) in toluene (20 ml) was heated under reflux within 60 minutes. The reaction mixture was then chilled and evaporated to dryness. The obtained yellow crystals of a crude product (0.5 g) were purified by chromatography over a silica gel column by the use of solvent system EtOAc:Me$_2$CO=1:1 yielding 0.14 g of 9(S)-N-(β-cyano-β-carbetoxyethenyl)erythromycylamine with the following physical-chemical constants:

IR ($CHCl_3$) cm$^{-1}$: 3500, 2950, 2200, 1730, 1675, 1625, 1450, 1380, 1250, 1225, 1170, 1080;

¹H NMR (300 MHz, CDCl₃) δ: 9.46 (1H, 9-NH—CH), 7.05 (9-NH—CH=C), 5.07 (1H, H-1"), 4.61 (1H, H-1'), 4.22 (1H, H-3), 4.19 (—COOCH₂CH₃), 3.76 (1H, H-5), 3.34 (3H, 3"-OCH₃), 3.25 (1H, H-2'), 2.29 [6H, 3'-N(CH₃)₂], 2.20 (1H, H-10), 1.96 (1H, H-8), 1.31 —COOCH₂CH₃), 1.14 (3H, 8-CH₃), 1.05 (3H, 10-CH₃);

¹³C NMR (75 MHz, CDCl₃) δ: 177.5 (C-1), 167.6 (—COOCH₂ CH₃) 159.1 (9-NH—CH=C), 119.4 (—CN), 117.5 (9-NH—CH=C), 101.7 (C-1'), 95.2 (C-1"), 80.8 (C-5), 78.9 (C-3), 60.1 (—COOCH₂CH₃), 77.5 (C-4"), 70.7 (C-2"), 75.5 (C-9), 49.1 (3"-OCH₃), 40.1 [3'-N(CH₃)₂], 32.1 (C-10), 32.7 (C-8), 18.4 (8-CH₃), 14.2 (—COOCH₂CH₃), 13.2 (10-CH₃);

FAB-MS m/z 858 (M+H)⁺.

EXAMPLE 3

9(S)-N-(β,β-diacetylethenyl)erythromycylamine

According to the process described in Example 2, by the reaction of 9(S)-erythromycylamine (0.5 g; 0.68 mmol) and ethoxymethylene acetyl acetone (1.0 ml; 6.88 mmol) in toluene (20 ml) under heating for 90 minutes at a temperature of 50° C. 0.54 g of a crude product were obtained. By chromatography over silica gel column using the solvent system EtOAc:Me₂CO=1:1 there were obtained 0.21 g of 9(S)-N-(β,β-diacetylethenyl) erythromycylamine with the following physical-chemical constants:

IR (CHCl₃) cm⁻¹: 3500, 2950,1725, 1610,1550, 1450, 1375, 1320, 1170, 1080;

¹H NMR (300 MHz, CDCl₃) δ: 10.89 (1H, 9-NH—CH), 5.14 (1H, H-1"), 4.71 (1H, H-1'), 3.84 (1H, H-3), 3.70 (1H, H-5), 3.35 (3H, 3"-OCH₃), 3.30 (1H, H-2'), 2.31 [6H, 3'-N(CH₃)₂], 2.21 (1H, H-10), 1.99 (1H, H-8), 1.96 (3H, —COCH₃), 1.87 (3H, —COCH₃), 1.20 (3H, 8-CH₃), 1.06 (3H, 10-CH₃);

¹³C NMR (75 MHz, CDCl₃) δ: 193.4 (—COCH₃), 176.8 (C-1), 163.1 (9-NH—CH=C), 101.9 (C-1'), 95.2 (C-1"), 79.1 (C-5), 78.2 (C-3), 77.6 (C-4"), 70.7 (C-2"), 65.5 (C-9), 48.9 (3"-OCH₃), 40.0 [3'N(CH₃)₂]32.9 (C-10), 33.4 (C-8), 28.2 (—COCH₃), 19.1 (—COCH₃), 18.3 (8-CH₃), 12.5 (10-CH₃).

EXAMPLE 4

9(S)-N-(β,β-dicyanoethenyl)erythromycylamine

A mixture of 9(S)-erythromycylamine (0.5 g; 0.68 mmol) and ethoxy methylene malone dinitryl (0.18 g; 1.47 mmol) in toluene (20 ml) was stirred at a room temperature for about 30 minutes. The cooled reaction mixture was evaporated and the obtained yellow crystals (0.65 g) were purified by chromatography over a silica gel column using the solvent system CHCl₃: MeOH=9:1 yielding 0.26 g of 9(S)-N-(β,β-dicyanoethenyl) erythromycylamine with the following physical-chemical constants:

IR (CHCl₃) cm⁻¹: 3500, 2950, 2200, 1725, 1625, 1550, 1450, 1375, 1320, 1175, 1050, 750;

¹H NMR (300 MHz, CDCl₃) δ: 8.22 (1H, 9-NH—CH), 7.13 (1H,9-NH—CH=), 5.04 (1H, H-1"), 4.59 (1H, H-1'), 3.82 (1H, H-3), 3.68 (1H, H-5), 3.29 (3H, 3"-OCH₃), 3.23 (1H, H-2'), 2.31 [6H, 3'-N(CH₃)₂], 2.22 (1H, H-10), 1.94 (1H, H-8), 1.13 (3H, 8-CH₃), 1.05 (3H, 10-CH₃);

¹³C NMR (75 MHz, CDCl₃) δ: 177.1 (C-1), 160.4 (9-NH—CH=), 132.2 (9-NH—CH=C), 116.1 (—CN), 114.6 (—CN), 101.6 (C-1') 95.4 (C-1"), 80.8 (C-5), 78.9 (C-3), 77.3 (C-4"), 70.5 (C-2'), 74.4 (C-9), 49.0 (3"-OCH₃), 40.0 [3'-N(CH₃)₂], 31.8 (C-10), 32.5 (C-8), 18.9 (8-CH₃), 13.6 (10-CH₃);

FAB-MS m/z 811.5 (M+H)⁺.

EXAMPLE 5

9(S)-N-(β-acetyl-β-carbetoxyethenyl)erythromycylamine

According to the process described in Example 4 by the reaction of 9(S)-erythromycylamine (0.5 g; 0.68 mmol) and ethyl-α-(etoxymethylene)-acetoacetate (1.0 ml; 5.77 mmol) in toluene (20 ml) there were obtained 0.54 g of a resin residue. Chromatography over silica gel column using the solvent system CHCl₃:MeOH=9:1 gave 0.29 g of 9(S)-N-(β-acetyl-β-carbetoxyethenyl)erythromycylamine with the following physical-chemical constants:

IR (CHCl₃) cm⁻¹ 3500, 2950, 1725, 1680, 1640, 1570, 1450, 1380, 1250, 1170, 1080;

¹H NMR (300 MHz, CDCl₃) δ: 11.15 (1H, 9-NH—CH=), 7.74 (1H,9-NH—CH=), 5.11 (1H, H-1"), 4.74 (1H, H-1'), 4.21 (1H, H-3), 3.71 (1H, H-5), 4.18 (3H, —COOCH₂CH₃), 3.34 (3H, 3"-OCH₃), 3.24 (1H, H-5), 2.45 (3H, —COCH₃), 3.23 (1H, H-2'), 2.34 [6H, 3'-N(CH₃)₂], 2.22 (1H, H-10), 1.94 (1H, H-8), 1.27 (3H, —COOCH₂CH₃), 1.15 (3H, 8-CH3), 1.04 (3H, 10-CH₃);

¹³C NMR (75 MHz, CDCl₃) δ: 198.5 (—COCH₃), 177.1 (C-1), 167.7 (—COOCH₂CH₃), 159.8 (9-NH—CH=), 132.2 (9-NH—CH=C), 101.7 (C-1'), 95.3 (C-1"), 80.9 (C-5), 78.8 (C-3), 58.9 (—COOCHhd 2CH₃), 77.4 (C-4"), 70.5 (C-2'), 75.1 (C-9), 48.8 (3"-OCH₃), 39.9 [3'-N(CH₃)₂], 32.1 (C-10), 33.2 (C-8), 30.4 (—COCH₃), 18.1 (8-CH₃), 14.0 (—COOCH₂CH₃), 12.9 (10-CH₃);

FAB-MS m/z 875.2 (M+H)⁺.

We claim:

1. 9-N-Ethenyl derivatives of 9(S)-erythromycylamine of the general formula (I)

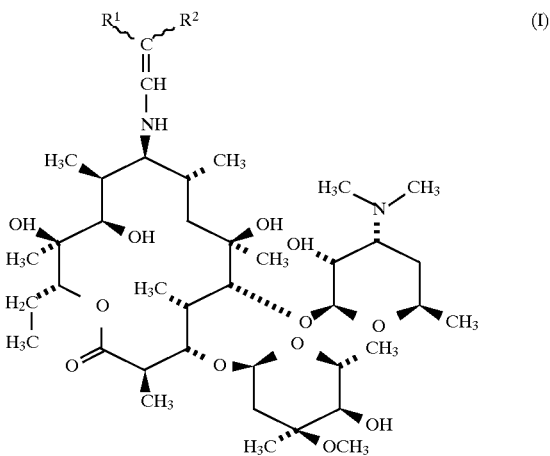

wherein R¹ and R² are the same or different and represent nitryl, a carboxyl group of the formula COOR³, wherein R³ represents a C₁–C₄ alkyl group, or a keto group of the formula COR⁴, wherein R⁴ represents a C₁–C₄ alkyl group, and pharmaceutically acceptable addition salts thereof with inorganic or organic acids.

2. A substance according to claim 1, wherein R¹ and R² are the same or different and represent carboxyl group of the formula COOR³.

3. A substance according to claim 2, wherein R³ represents a C₁–C₄ alkyl group.

4. A substance according to claim 3, wherein the C₁–C₄ alkyl group is ethyl group.

5. A substance according to claim 1, wherein one of $R^1$ and $R^2$ represents nitryl and the other of $R^1$ and $R^2$ represents a carboxyl group of the formula $COOR^3$.

6. A substance according to claim 5, wherein $R^3$ represents a $C_1$–$C_4$ alkyl group.

7. A substance according to claim 6, wherein the $C_1$–$C_4$ alkyl group is ethyl group.

8. A substance according to claim 1, wherein $R^1$ and $R^2$ are the same and represent a keto group of the formula $COR^4$.

9. A substance according to claim 8, wherein $R^4$ represents a $C_1$–$C_4$ alkyl group.

10. A substance according to claim 9, wherein the $C_1$–$C_4$ alkyl group is methyl group.

11. A substance according to claim 1, wherein $R^1$ and $R^2$ are the same and represent nitryl.

12. A substance according to claim 1, wherein one of $R^1$ and $R^2$ represents a carboxyl group of the formula $COOR^3$ and the other one of $R^1$ and $R^2$ represents a keto group of the formula $COR^4$.

13. A substance according to claim 12, wherein $R^3$ represents a $C_1$–$C_4$ alkyl group.

14. A substance according to claim 13, wherein the $C_1$–$C_4$ alkyl group is ethyl group.

15. A substance according to claim 12, wherein $R^4$ represents a $C_1$–$C_4$ alkyl group.

16. A substance according to claim 15, wherein the $C_1$–$C_4$ alkyl group is methyl group.

17. A process for the preparation of 9-N-Ethenyl derivatives of 9(S)-erythro-mycylamine of the formula (I)

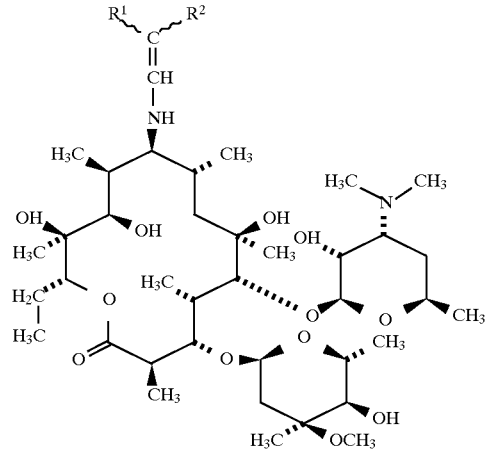

wherein $R^1$ and $R^2$ are the same or different and represent nitryl, a carboxy group of the formula $COOR^3$, wherein $R^3$ represents $C_1$–$C_4$ alkyl group, or a keto group of the formula $COR^4$, wherein $R^4$ represents a $C_1$–$C_4$ alkyl group, and of pharmaceutically acceptable addition salts thereof with inorganic or organic acids, wherein 9(S)-erythromycylarnine of the formula (II)

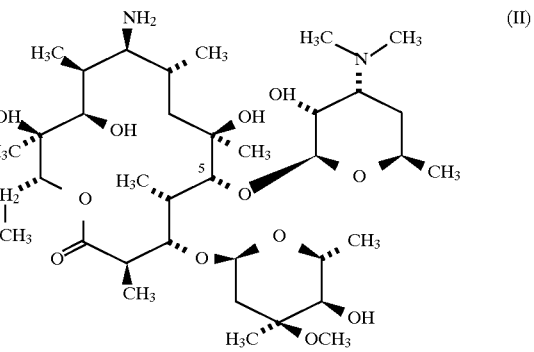

is subjected to a reaction with ethoxyethylene derivatives of the formula (III)

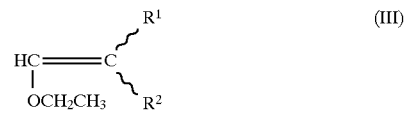

wherein $R^1$ and $R^2$ are the same or different and represent nitryl, a carboxyl group of the formula $COOR^3$, wherein $R^3$ represents a $C_1$–$C_4$ alkyl group, or a keto group of the formula $COR^4$, wherein $R^4$ represents $C_1$–$C_4$ alkyl group, in toluene, xylene or another aprotic solvent at a temperature from 20° to 80° C. and then, optimally to a reaction with inorganic or organic acids.

18. A pharmaceutical composition comprising a pharmaceutically acceptable carrier and an antibacterially effective amount of substances according to claim 1.

* * * * *